United States Patent
Ritsche et al.

(10) Patent No.: US 6,626,328 B2
(45) Date of Patent: Sep. 30, 2003

(54) MEDIA DISPENSER

(75) Inventors: Stefan Ritsche, Radolfzell (DE); Juergen Greiner-Perth, Gottmadingen (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/738,706

(22) Filed: Dec. 15, 2000

(65) Prior Publication Data

US 2001/0007327 A1 Jul. 12, 2001

(30) Foreign Application Priority Data

Dec. 15, 1999 (DE) .......................... 199 60 459

(51) Int. Cl.[7] .......................... B67D 5/00; A61M 15/08
(52) U.S. Cl. .......................... 222/82; 222/83; 222/83.5; 222/129; 222/327; 222/321.1; 222/387
(58) Field of Search .......................... 222/82, 83, 88, 222/83.5, 129, 327, 321.1, 387

(56) References Cited

U.S. PATENT DOCUMENTS

| | | | | |
|---|---|---|---|---|
| 2,904,043 A | * | 9/1959 | Friedman ................ 604/228 |
| 3,884,229 A | * | 5/1975 | Raines et al. ............. 604/232 |
| 4,445,895 A | * | 5/1984 | Margulies ................ 604/193 |
| 5,437,398 A | | 8/1995 | Ritsche .................. 222/321.8 |
| 5,472,422 A | * | 12/1995 | Ljungquist ............... 604/89 |
| 5,509,578 A | * | 4/1996 | Livingstone ............ 222/321.6 |
| 5,549,561 A | * | 8/1996 | Jjertman ................. 604/179 |
| 5,716,338 A | * | 2/1998 | Hjertman et al. .......... 604/191 |
| 5,927,559 A | | 7/1999 | Bommer et al. .......... 222/189.09 |
| 5,967,369 A | | 10/1999 | Kafer et al. .............. 222/82 |
| 6,145,703 A | * | 11/2000 | Opperman ............ 222/153.13 |

FOREIGN PATENT DOCUMENTS

| DE | 35 25 449 A1 | 1/1987 |
|---|---|---|
| DE | 197 39 990 A1 | 3/1999 |

* cited by examiner

Primary Examiner—Kenneth Bomberg
(74) Attorney, Agent, or Firm—Quarles & Brady LLP

(57) ABSTRACT

A dispenser (1) comprises a reservoir (7) and a plunger pump (8), the medium inlet (3) of which pierces a closure (45) of the reservoir (7), after which the medium can be discharged metered from the reservoir (7) by repeated strokes with the pump (8). Until used the medium thus remains hermetically sealed.

16 Claims, 2 Drawing Sheets

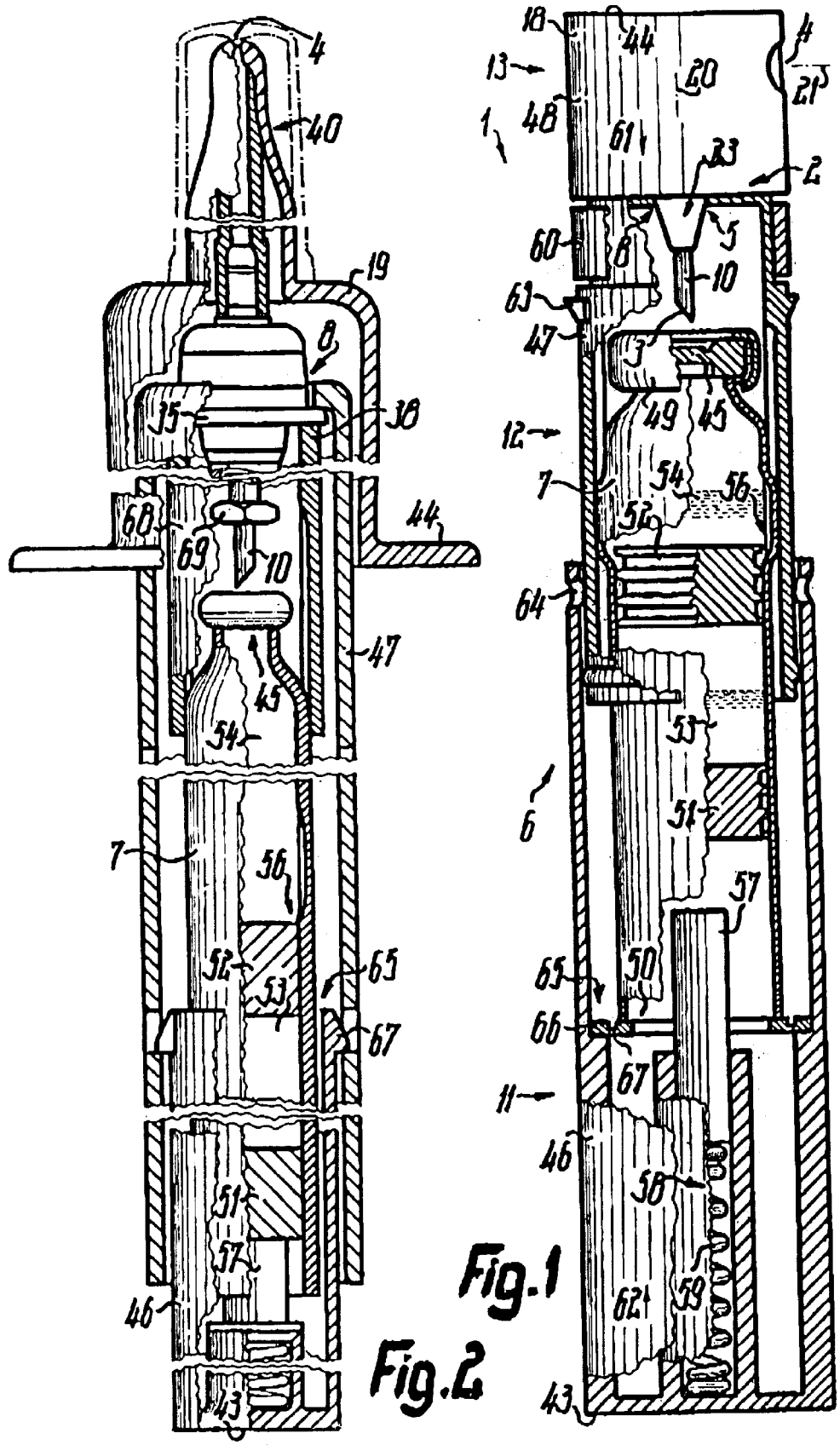

MEDIA DISPENSER

TECHNICAL FIELD AND BACKGROUND OF THE INVENTION

The invention relates to a dispenser suitable for discharging or storing particulate media, a flowable medium. Each of these media may be liquid, pasty, powdery and/or gaseous.

In medical hypodermic syringes or the like, the dispenser comprises a barrel including a piston and an injection needle serving both as an inlet and outlet for the medium. In contrast thereto, in the invention the passages are separate or spaced away from each other, e.g. at ends of a body facing away from each other, through which the medium flows and which may be a valve or pump body. This body may comprise three, four or more inner widths each differing from the other and offset from each other and house at least two, three or more components internally. In addition, the body comprises means, such as a flange for connecting a base which may be solely a medium reservoir or comprise a medium reservoir.

SUMMARY OF THE INVENTION

The invention is based on the object of providing a dispenser which avoids the disadvantages of known configurations and the cited hypodermic syringes. More particularly it is intended that at least one of the medium passages is suitable for piercing diaphragms, tissue or the like. Furthermore, closures or walls are intended to be opened by the dispenser by simple ways and means. Handling of the dispenser is simplified.

In accordance with the invention, the body comprises a freely protruding piercing or opening member, such as a hollow or pointed piercing needle, which is made of a material whose properties correspond to those of steel or hardened steel. The piercing member may have an outer width of less than 2 mm or a wall thickness which is greater than half or two-thirds of the inner width. When the piercing member is used as the outlet, the dispenser can be used as a syringe. When used as an inlet the dispenser can be sealingly connected by the piercing action to a medication cartridge, such as a carpule. Although the piercing member could be mounted to be movable on the body in overcoming a spring force, it is however expediently and non-releasably connected thereto, e.g. by the injection molding action when the body is molded in a plastics material. All parts of the dispenser with the exception of one or more springs may be injection molded or formed of plastics parts. The dispenser is designed for holding and simultaneous actuation of all of its functions with one hand.

The body is advantageously provided with communicating paths for the medium, at least one of which is variable in its length or cross-section. For this purpose a piston, a valve or some other control element may be provided in the body. Preferably the dispenser comprises a pump, such as a plunger pump comprising one or more manually actuatable valves or one or more pressure relief valves.

It is particularly advantageous when the body and a medium reservoir forms a preassembly so that in the starting position the piercing member has yet to open the reservoir, it not being until manually actuated that the reservoir is first opened and subsequently the medium exchanged between the reservoir and the body due to both then intercommunicating.

The outlet may be configured for dispensing droplets, a jet of the medium, or as an atomizing nozzle. Preferably the outlet is provided in a nozzle suitable for insertion into a body opening of a patient.

The body or the element provided for penetration of the piercing member may be shielded outwardly partly, mostly or totally so that protection from damage is assured. Each piston of the dispenser may be a valve and/or a displacement element.

The dispenser advantageously comprises two finger rests located transversely to the direction of the stroke and spaced away from each other. The finger rests approach each other on actuation and are suitable for both the piercing stroke and a pumping stroke or for a filling stroke by which the medium in the reservoir is communicated into the region of the medium inlet. Each of these strokes may be counteracted by a restraint at the start of the stroke which can be defeated by a sudden increased actuating force, after which the forces counteracting the further actuatation are instantaneously many times less than the restraining forces to thus permit high flow rates of the medium or a high impingement velocity of the piercing member on piercing.

Piercing may require overcoming a spring force independently of the piercing cross-section to thus preserve the piercing member and the piercing cross-section due to piercing being attentuated by the spring force and is also powered when the spring force is sufficiently high. Advantageously, however, the spring is rigidly supported and is only the element to be pierced is elastic.

Reference is made to the German patents pending 196 10 457, 197 39 990 and 196 37 101 for further description of the operational effects of a dispenser made according to the present invention.

These and further features read not only from the claims but also from the description and the drawings. Each of the individual features is achieved by itself or severally in the form of sub-combinations in one embodiment of the invention and in other fields and may represent advantageous aspects as well as being patentable in its own right, for which protection is sought in the present. The division of the application into sections including sub-titling does not restrict the general validity of the comments made thereunder.

BRIEF DESCRIPTION OF THE DRAWINGS

Example embodiments of the invention are explained in more detail in the following and illustrated in the drawings in which:

FIG. 1 is an axial section in part through the dispenser in accordance with the invention, FIG. 2 is an illustration of a further embodiment of that as shown in FIG. 1

DETAILED DESCRIPTION

Figure 3:
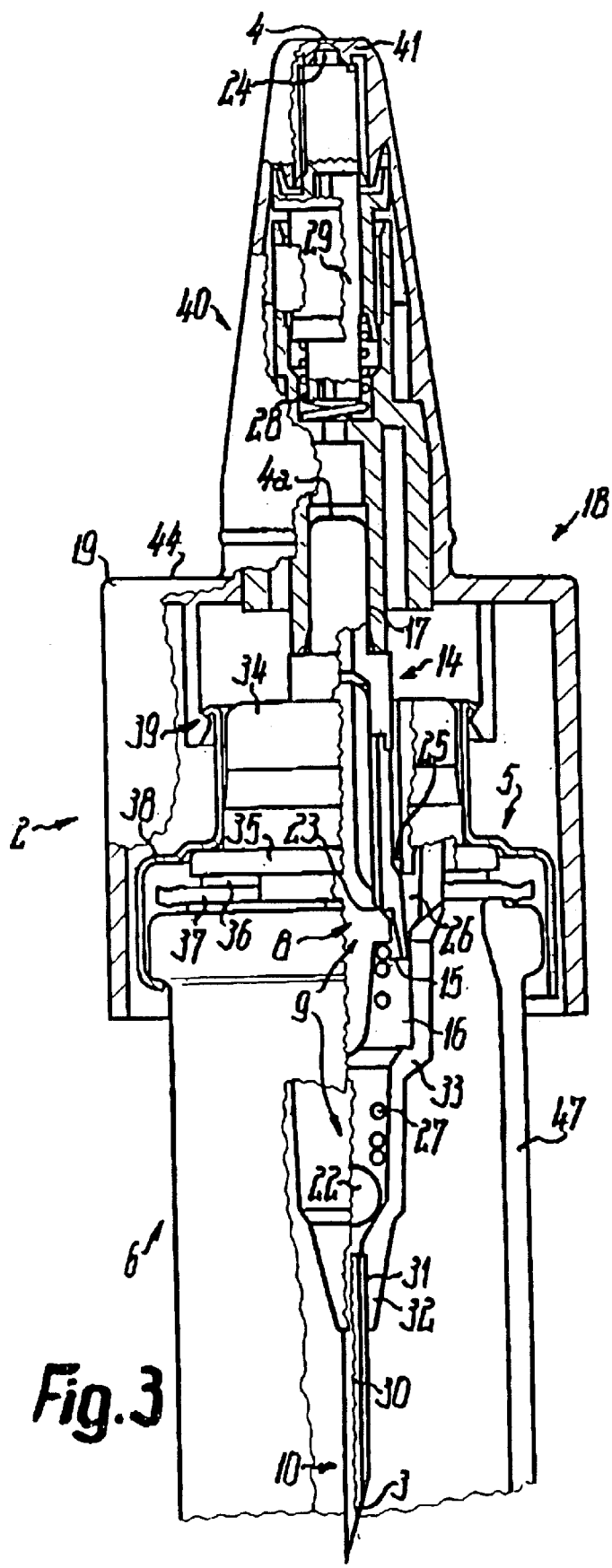
FIG. 3 is an illustration of a third embodiment.

Referring now to FIGS. 1–3, there is illustrated a dispenser 1 containing a body 2 comprising as medium passages at one end an inlet 3 and at the other end one or more outlets 4, 4a for the media. The body 2 is rigidly secured by the connecting means 5 on a base 6 to a part of the body. The base 6 may comprise a hollow element 7, such as a medium reservoir or a medication cartridge or carpule, or may be formed simply by this hollow or otherwise configured element. The body 2 comprises a pump 8 or plunger pump, as well as a closure or valve assembly 9, and a piercing member 10, the latter being a hollow needle of metal whose proximal end forms a sharp tip with a slanting or oval face adjoining the outer circumference which is cylindrical throughout. The inlet 3 is thus located at an acute angle or transversely to the longitudinal centerline of the needle.

The dispenser 1 comprises a longitudinal train of three units 11 to 13 of which the second unit 12 is movable relative to the first unit 11 and the third unit 13 is movable relative to the second unit 12 and together therewith is movable relative to the first unit 11, in an axially shiftable direction. The second unit 12 supports the reservoir 7 while stationary, and when moved in an axial direction, the cited part of the body 2 belonging to the second unit 12. One advantageous and detailed configuration of the pump 8 is evident in detail from FIG. 3. The cited body part consists of an integral elongated main element 33 and an integral, as well as shorter, cover 34 forming a pump or valve body.

A piston unit 14 is provided for axial movement in this body 33, 34. The piston unit 14 including a piston 15 sealingly sliding along the inner circumference of the body and defining a variable-volume chamber such as a pumping chamber 16. The plunger 17 of the piston unit 14 adjoining the piston 15 protrudes through the cover 34 from the body 33, 34 and is fixedly connected via a connector to a head 18 serving as the actuatable discharge head. The cited parts are located along the longitudinal centerline 20 of the dispenser 1 to which the axis 21 of the outlet 4 which ports into the environment, as shown in FIG. 1. The outlet may be located transversely or at right angles, or as shown in FIGS. 2 and 3, parallel thereto or along the same axis. This outlet 4 is provided at the circumference of the head 18 or at the free end thereof.

The valve assembly 9 comprises in the body 33, 34 an inlet valve 22 located between the chamber 16 and the secured end of the cannula or needle 10. Also located in the body 33, 34 is an outlet valve 23, the two valve elements of which a rearranged on the unit 14. The movable valve element is formed by the inner circumference of the hollow piston 15 whose sleeve shank forms the valve spring for closing the valve. Also located within the body 33, 34 is a vent valve 25 of a vent 26 for venting the reservoir should the reservoir space thereof not be variable in volume. The movable valve element of the vent valve 25 is likewise formed by the piston 15 while the valve seat is formed by the body or its cover 34. Air is able to flow from the environment along the plunger 17 into the body 33, 34 and from there through an opening in the body wall into the reservoir.

Provided furthermore in the head 18 of the variable-length body 2 is an outlet valve 24, the valve element of which is located directly adjoining the outlet 4. As shown in FIGS. 1 to 3, the piston unit 14 is spring-loaded in the starting position by a return spring 27 located in the chamber 16. In the starting position the unit 14 is positively located by a stop or closing of the vent valve 25 so that when the stroke commences, the vent valve 25 opens. The outlet valve 24 is closed by a spring 28. Each of the valves 22 to 25 may be a pressure relief valve or a valve that is manually actuatable by a stroke as well as closing by stopper action at its valve faces or may configured as a spool valve. At the valve 23, the piston unit 14 or the plunger 17 is penetrated internally by an outlet passage 29, the end of which forms the outlet. The plunger connection with the head 18 can be released and withdrawn in an axial direction, the outlet 4a at the end of the plunger 17 being located within the head 18.

The needle bore of the member 10 forms an inlet passage 30 for communicating with the reservoir 7 via the opening 3, the inlet passage 30 directly porting against the valve element, such as a ball of the valve 22 and thus directly porting into the chamber 16 when valve 22 is open. The inner, shorter end of the piercing member 10 is rigidly secured to the main element 33 by a fastener 31, and is surrounded by the inner end section 32 of the main element 33 and is supported against thrust loads by being positively stopped by its inner end surface area. The main element 33 of the body including the piercing member 10 protrudes along the majority of its length, as well as at the outer circumference, into the unit 12 without contacting the latter.

The cover 34 is non-releasably connected to the flared end of the element 33 by a snapper and is located by the majority of its length outside of the unit 12. The body or cover 34 is provided with a radially protruding annular flange 35 with which the body 33, 34 is axially tensioned against an end surface area of the unit 12. A seal 36 or a filter 37 may be clamped in place between the flange 35 and this end surface area, this filter 37 likewise enabling the reservoir 7, as described, to be vented. A fastener such as a crimp ring or an outer sleeve of the unit 12 is provided for tensioning. The head 18 is prevented from being pulled off from the piston unit 14 or from the body 33, 34 by a positive lock 39 located within the cap 19 of the head 18 or totally within the body 2. As shown in FIGS. 2 and 3 the head 18 comprises a freely protruding nozzle 40 for introducing into a bodily opening, such as a nostril. The end of the nozzle 40 is formed by a face wall 41 which is penetrated by the outlet passage 29 or outlet 4. As evident from FIG. 1, the shell of the cap of the head 18 is penetrated in this way, the face wall of the cap forming the finger rest 44. The nozzle 40 protrudes integrally from the face wall of the cap 19 so that the finger rest 44 is located on both sides of the nozzle 40. The other finger rest 43 is formed by the end of the unit 11 facing away from the finger rest 44.

The tip of the needle 10 is located slightly spaced away from the reservoir 7 or axially opposite one of the walls or the like. This wall is a closure or a diaphragm 45 sealingly closing off the discharge opening of the reservoir 7 and locked and tensioned in place by an annular fastener such as a crimp ring 49. The diaphragm 45 is made of flexible rubber several millimeters thick and may be reduced in thickness in the region to be pierced. The diaphragm 45 is inserted in a constricted neck of the reservoir 7 and tensioned against a shoulder ring in the interior of this neck, the crimp ring 49 being located at the outer circumference without contacting it. The end 50 of the reservoir 7 facing away from the diaphragm 45 is open to a degree which is constant up to the neck so that the inner circumference forms a runway for closure members or pistons 51, 52.

Between the two pistons 51, 52 a chamber 53, and between piston 52 and diaphragm 45 a medium space 54, are each sealingly defined in the interior of the reservoir 7. Each of the chambers 53, 54 may be filled with one of the cited media totally or partly or up to half full. A closure to be opened or a valve 56 serves to allow flow and communication between the two chambers 53, 54 e.g. so that the medium can be transferred from the chamber 53 further removed from the closure 45 into the chamber 54 by a single stroke in a single direction when the outlet 4 is located in an upward direction. The valve 56 is a spool valve, and has a shiftable valve element which forms the piston 52, and which at the inner circumference of the reservoir 7 comprises bypass channels for connecting the chambers 53, 54.

The exposed outer surface area of the units 11 to 13 is formed by a sleeve or by cap-shaped single elements 46 to 48 which can be shiftingly telescoped into each other. As shown in FIG. 1 the single elements 46, 48 of the units 11, 13 surround the ends facing away from each other of the single element 47 of the unit 12 which can be totally nested in the single elements 46, 48. As shown in FIG. 2, the single element 46 engages the interior of the unit 12. Each of the single elements 46 to 48 is configured as an integral component. The circumferential surface areas facing each other of the interengaging single elements are guided in a sliding seal or slightly spaced away from each other. The element 46 comprises internally a plunger 57 oriented against the piston 51, which in the starting position as shown in FIG. 1, is located spaced away from the piston 51 and, as shown in FIG. 2, is in contact with the piston 51. The plunger 57 protrudes into the end 50 without contacting it, and is axially shiftable in a sliding guide or sleeve of the element 46, namely in overcoming the force of the compression spring 59 belonging to the spring means 58 which may also include the compressible gas or air supplies in the chambers 53, 54.

Depending on the requirements, the diaphragm 45 is pierced on a filling stroke and then with a subsequent stroke in the same direction the medium is transferred from the chamber 53 into the chamber 54 or, in special circumstances first the medium is transferred before the diaphragm 45 is pierced.

As evident from FIG. 1, squeezing both finger rests 43, 44 first shifts the unit 11 and shortens the length of the dispenser 1 in the direction 62 until the reservoir 7 has been slaved in the proximal movement to such an extent that the piercing member 10 has pierced the diaphragm 45, it not being until then that the plunger 57 is released or moved relative to the reservoir 7 until it comes up against the piston 51, slaving it in its movement. Once the chamber 53 has been totally filled with non-compressible fluid or with the presence of a corresponding slaving element the piston 52 is simultaneously slaved in the movement of the piston 51. When the filling of the chamber 53 is partly compressible or when some other flexible connection exists between the pistons, the piston 52 first remains stationary until a sufficiently high compressive or spring tension has been achieved, it not being until the chamber 53 has been reduced in size that also the piston 52 is slaved in the movement. This results in the piston 52 attaining a position in which the valve 56 is opened and the piston 51 is urged further until it comes up against the piston 52 so that the medium is transferred from the chamber 53 totally into the chamber 54 where it mixed with the medium contained therein or forms a solution therewith.

This stroke can now be terminated or further continued to compress the medium in the chamber 54. The spring means 58 damp this stroke whereby the compression spring 59 is pretensioned and the piston 51 is urged with a delay relative to the stroke 62. Once the unit 11 has attained the corresponding end position before the piston 51, or in advance movement before that of the piston 51, the transfer velocity is dictated by the compression spring 59 to avoid excessively high pressures in the chamber 54. At the end of this stroke the units 11, 12 are interlocked, e.g. by radially flexible snappers 63 of the element 47 which automatically snap into place in complementary members 64 such as openings in the shell of the element 46 and are then tensioned with zero clearance by the compression spring 59. The lock 39 is also able to move the piston 51 only until it contacts the piston 52 without slaving the body 2 in its movement. As a result, due to totally emptying of the chamber 53, an optimum mixing ratio of the media is attained. The compression spring 59 is, however, also able to move the piston sufficiently in the direction 62 so that the chamber has a precisely predefined volume which then corresponds to the rated delivery to be dispensed by the dispenser. On this movement the air is totally expelled from the chamber 54 the same as any volume of the non-gaseous medium or mixture exceeding the rated delivery. For this purpose the travel of the plunger 57 in the direction 62 may be directly defined by the stop, e.g. with a flexible snapper engaging a longitudinal guide in the sliding sleeve. The spring 59 is then also tensioned in this end or stop position. The stop may also act directly on the spring 59.

During the stroke 62 the unit 13 is blocked from being actuatable in the opposite direction. A positive lock or block is provided for this purpose between the open end of the cap 18, 48 and the locking member 63. The locking member 60 is a ring or a sleeve snugly surrounding the element 47 and can be sheared off or radially pulled off so that it is also suitable to thwart tampering. A correspond lock 65 affects the sequence of functions as described and also opposes the stroke 62. As shown in FIG. 1 the lock 65 first slaves the reservoir 7 in its movement until the diaphragm 45 has been pierced so that the lock 65 can then be defeated by applying a sufficiently high actuating force instantly resulting in a substantially smaller resistance being offered to the stroke 62 up to the end of the stroke. The locking member 66 of the chamber 54 is a ring surrounding the plunger 57 and comprises a weakened zone or frangible location 67 spaced away from and between its outer and inner circumference. The ring part located outside of the frangible location 67 is supported against movements in the direction 61 by an inner shoulder of the element 46 and the inner ring part is supported against movements in the direction 62 by the end surface area of the reservoir 7. Once the travel of the stroke 62 in opening the diaphragm has been completed, after which the needle 10 is defined relative to the diaphragm 45, the inner ring part shears from the outer ring part at the frangible location 67 following initial flexible deformation and the plunger 57 commences its stroke in the direction 62.

In the first portion of the stroke 62 the reservoir 7 is thus shifted in the direction 62 prior to the locking member 60 being released, the needle 10 piercing the diaphragm 45 without contacting the member 59 to thus allow the inlet 3 to communicate with the chamber 54. During the shifting movement the reservoir 7 is slidingly guided by the inner circumference of the element 47, it executing a purely axial or also a rotative helical movement. For this purpose the wall of the reservoir 7 of constant thickness forms radially protruding cams in the region of the valve 56, which are guided in axial or steep helical grooves in the inner circumference of the element 47.

Once the lock 60 has been released, the element 48 including the piston unit 14 can then be moved relative to the units 11, 12, 33, 34 in the direction 61. The piston unit is moved with a further shortening of the dispenser 1 over a pumping or valve-opening stroke with the finger rests 43, 44 being actuated so that the chamber 16 is made smaller and exhausted before then being filled with part of the medium from the chamber 54 on the return stroke. The return stroke is powered by the return spring 27 through the passage 30 and with opening of the valve 23. On the next stroke 61 the medium is compressed in the chamber 16, as a result of which, the valve 22 closes while valve 23 is opened and the medium is propelled by the piston 15 and the plunger 17 into the interior of the head 18 as well as up to valve 24. The valve 24 opens in being response to the pressure of the medium, namely by movement of the internal valve element in the direction 61 whereas the opening movement of the valve element of valve 23 is opposed. After each return stroke, the chamber 16 is refilled from chamber 54 and on each subsequent stroke the thus metered amount of medium is discharged from the outlet 4.

Referring now to FIG. 2 there is illustrated how first the unit 13 is moved over the stroke 61 to thus make chamber 16 smaller and exhaust it, it not being until then that the transfer fill or the piercing of the diaphragm 45 can take place. Expediently, first the reservoir 7 is slaved in the movement in direction 62 and the diaphragm 45 is pierced by the needle 10, after which a transfer filling of the chamber 54 occurs. The finger rest 43 is then located in the plane of the corresponding end of element 47 into which element 46 has been totally nested. Releasing the finger rest 44 then causes the pump 8 to execute the return stroke and chamber 16 is instantly filled with the medium from chamber 54. Opening the diaphragm 45 prevents an excessive pressure or overpressure materializing in chamber 54 which would be communicated by the valve 56 into chamber 53.

As shown in FIG. 2 the fastener 38 is formed by a separate member 68, such as a sleeve, which tensions the flange 35 in the direction 62 against an inner ring shoulder at the end of the element 47 and is defined (not shown) relative to the element 47. At the inner circumference of the sleeve 68 the reservoir 7 is shiftingly guided. To define the piercing depth of the needle 10 a stop 69 may protrude beyond the outer circumference thereof, the needle coming up against the outer face of the diaphragm 45 at the end of the pumping stroke flexibly. The restraint 65 in this case is formed by the snappers 67 of the element 46 engaging openings in the shell of the element 47 and which in the starting position positively prevent the elements 46, 47 from being pulled apart.

All features of each embodiment may also be provided in any other embodiment and thus all passages of the description apply in sense to all embodiments. The features and effects may be provided precisely or only substantially or roughly as cited and may deviate more therefrom depending on the requirements. The reservoir 7 of the dispenser 1 permits storage of the medium hermetically sealed until used.

What is claimed is:

1. A media dispenser comprising:
   a base having a first base part and a second base part, being movable relative to each other;
   a pump assembly disposed on said second base part and movable relative to said second base part, said pump assembly having an inlet and an outlet, the inlet being provided with a piercing member;
   a reservoir housed in said base and having a first medium chamber and a second medium chamber, for containing first and second media, respectively, said reservoir also having a first piston and a second piston, the first medium chamber being bounded by the first piston and the second piston, both of said first piston and said second piston being arranged to be shifted in said reservoir, and the second medium chamber being bounded by the second piston and a diaphragm arranged to be pierced by said piercing member on a shifting and piercing stroke in order to connect the second chamber with the pump assembly;
   a valve, disposed between the first chamber and the second chamber, said valve being opened upon shifting of the second piston, thereby opening a flow path between the first chamber and the second chamber and allowing mixing of the first and second media; and
   interlocking members positioned on the first base part and the second base part to engage and secure the first base part and the second base part to each other upon completion of a shifting and mixing stroke of the first base part relative to the second base part which causes the opening of the valve and the mixing of media from the first medium chamber and the second medium chamber.

2. The dispenser as set forth in claim 1, wherein said interlocking members include a snap action member.

3. The dispenser as set forth in claim 1, wherein the interlocking members are provided to prevent withdrawal of the first base part from the second base part.

4. The dispenser as set forth in claim 1, wherein a locking member is provided to restrict movement of the pump assembly relative to the reservoir and the second base part.

5. The dispenser as set forth in claim 4, wherein the locking member is a removable ring interposed between the pump and the second base part.

6. The dispenser as set forth in claim 1, wherein said piercing member is a hollow metal needle, having a piercing tip.

7. The dispenser as set forth in claim 1, wherein for moving said piercing member said base comprises said first base part and said second base part mutually shiftable over a stroke, and wherein said first base part supports said reservoir and said second base part supports said pump assembly.

8. The dispenser as set forth in claim 7, wherein said reservoir is shiftingly located on said first base part.

9. The dispenser as set forth in claim 7, wherein at least one restraint is provided between the first and second base parts, said restraint to be overcome upon starting of the movement of the first base part and the second base part relative to each other by a greater manual force than necessary for a following movement.

10. The dispenser as set forth in claim 1, wherein said reservoir is a medication cartridge, having an interior space, which is open at its end remote from said piercing member.

11. The dispenser as set forth in claim 10, wherein a plunger is movable into said interior space to move said first piston.

12. The dispenser as set forth in claim 11, wherein said plunger is provided on said first base part.

13. The dispenser as set forth in claim 1, wherein means for spring-loading said base are provided.

14. The dispenser as set forth in claim 13, wherein the spring loading means include a spring acting between said plunger and the first base part.

15. The dispenser as set forth in claim 14, wherein the volume of said first chamber and said second chamber of said reservoir is variable with the aid of the spring when said plunger is spring-loaded against said spring.

16. A media dispenser comprising:
   a base having a first base part and a second base part, being movable relative to each other;
   a reservoir housed in said base and having a first medium chamber and a second medium chamber, for containing first and second media, respectively, said reservoir also having a first piston and a second piston, the first medium chamber being bounded by the first piston and the second piston, and the second medium chamber being bounded by the second piston and a diaphragm, both pistons being arranged to be shifted in said reservoir;
   the first base part being provided to exert manual pressure onto said first piston to shift the first piston in said reservoir and to cause the second piston to be shifted;
   a valve, disposed between the first chamber and the second chamber, said valve being opened upon shifting of the second piston, thereby opening a flow path between the first chamber and the second chamber and allowing mixing of the first and second media;

a pump having an inlet and an outlet, the inlet being provided with a piercing member arranged to pierce the diaphragm in order to connect the second chamber with the pump; and interlocking members to lock the first base part and the second base parts to each other after opening said valve;

wherein at least one restraint is provided between the first and second base parts, said restraint to be overcome upon starting of the movement of the first base part and the second base part relative to each other by a greater manual force than necessary for the following movement;

wherein for moving said piercing member said base comprises said first base part and said second base part mutually shiftable over a stroke, and wherein said first base part supports said reservoir and said second base part supports said pump; and wherein the restraint includes a frangible portion.

* * * * *

UNITED STATES PATENT AND TRADEMARK OFFICE
CERTIFICATE OF CORRECTION

PATENT NO. : 6,626,328 B2  Page 1 of 1
DATED : September 30, 2003
INVENTOR(S) : Stefan Ritsche et al.

It is certified that error appears in the above-identified patent and that said Letters Patent is hereby corrected as shown below:

Column 3,
Line 35, "a rearranged" should read -- are arranged --.

Signed and Sealed this

Twentieth Day of April, 2004

JON W. DUDAS
*Acting Director of the United States Patent and Trademark Office*